United States Patent [19]

Mongeon

[11] Patent Number: 4,648,541
[45] Date of Patent: Mar. 10, 1987

[54] BONE STAPLER

[75] Inventor: Douglas R. Mongeon, Orange, Calif.

[73] Assignee: Minnesota Mining and Manufacturing Company, Saint Paul, Minn.

[21] Appl. No.: 806,759

[22] Filed: Dec. 9, 1985

[51] Int. Cl.⁴ ............................................. A61B 17/00
[52] U.S. Cl. ................................. 227/19; 227/DIG. 1
[58] Field of Search ....... 128/334 R; 227/19, DIG. 1, 227/21

[56] References Cited

U.S. PATENT DOCUMENTS

| 4,204,623 | 5/1980 | Green ................................... 227/19 |
| 4,403,693 | 9/1983 | Froehlich ......................... 227/19 X |
| 4,500,025 | 2/1985 | Skwor ................................... 227/19 |
| 4,527,726 | 7/1985 | Assell et al. .......................... 227/19 |
| 4,540,110 | 9/1985 | Bent ........................................ 227/8 |
| 4,569,469 | 2/1986 | Mongeon et al. .................... 227/19 |
| 4,596,350 | 6/1986 | Smith et al. .......................... 227/19 |

Primary Examiner—Paul A. Bell
Attorney, Agent, or Firm—Donald M. Sell; James A. Smith; William L. Huebsch

[57] ABSTRACT

A bone stapler having separable barrel and handle assemblies so that staples of different sizes may be driven, in which a driver engages or disengages a piston assembly upon relative rotation therebetween to engage housing portions of the barrel and handle assemblies, and the barrel assembly through which staples are driven can be rotated to any angle about its axis with respect to a manually grasped portion of the handle assembly to help orient the driven staple.

9 Claims, 9 Drawing Figures

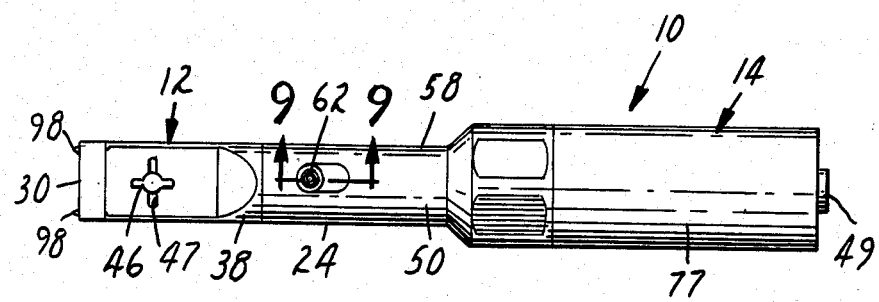
Fig. 1
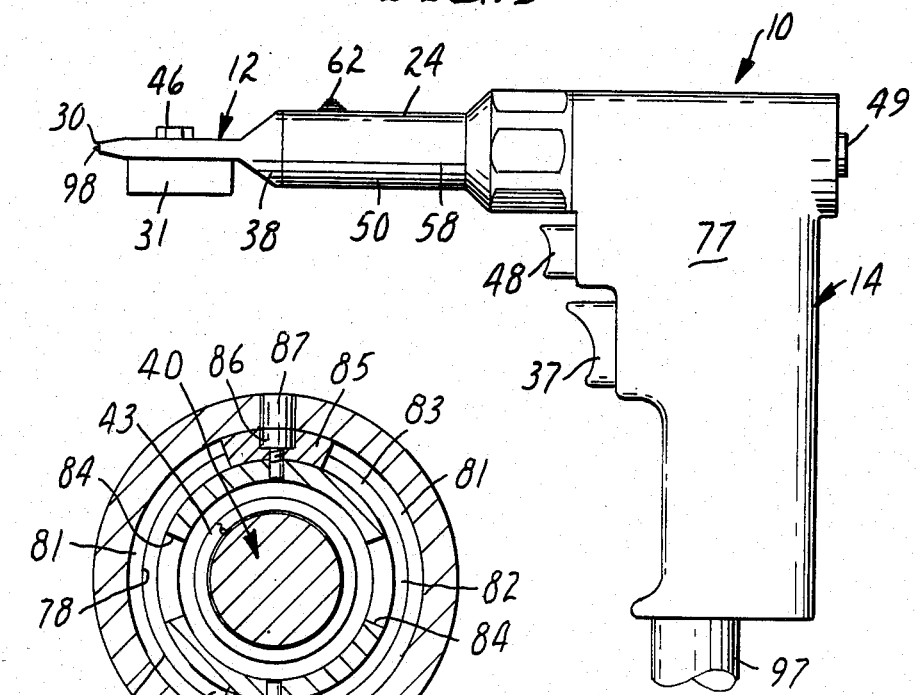
Fig. 8
Fig. 2

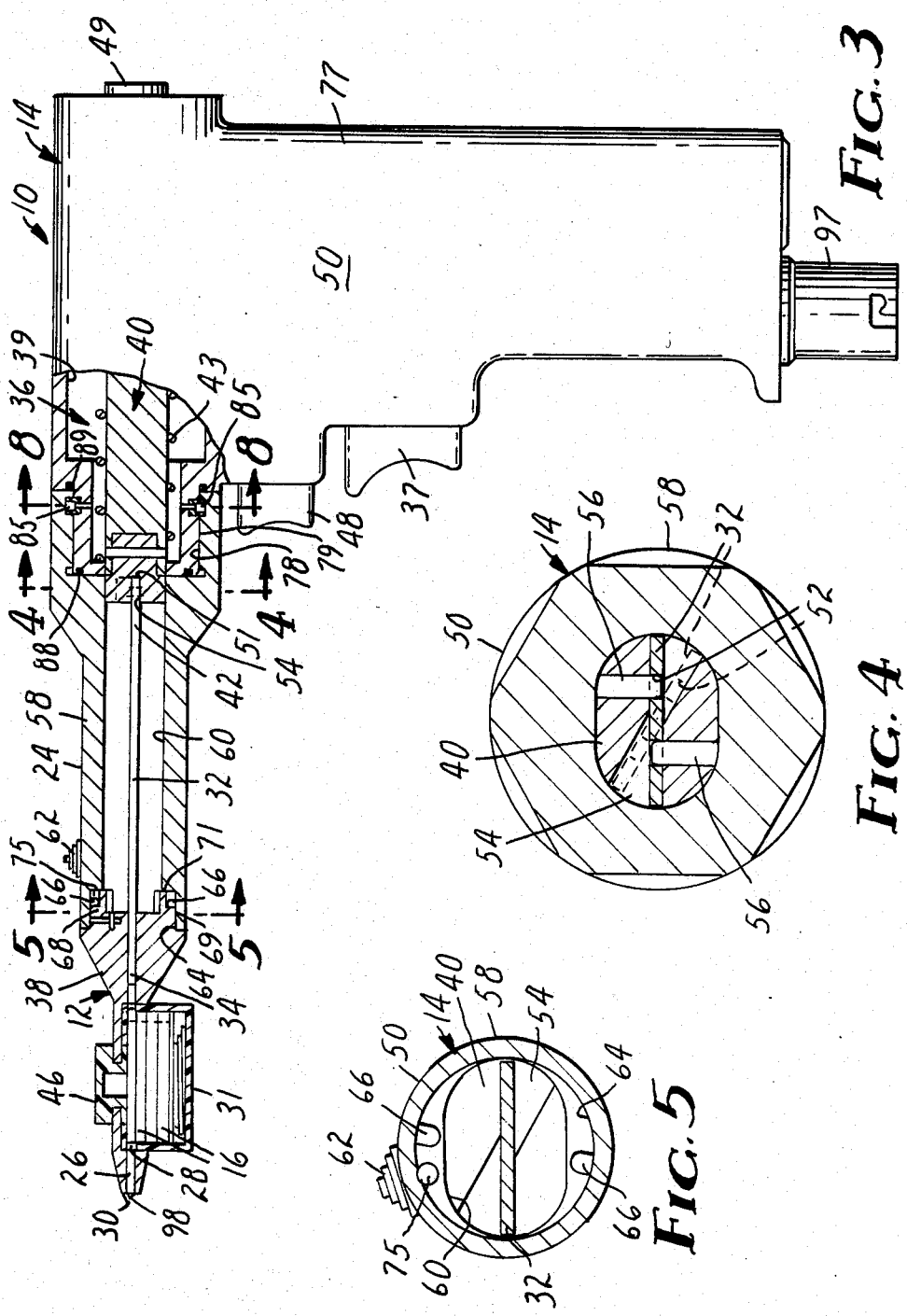

4,648,541

BONE STAPLER

TECHNICAL FIELD

This invention relates to devices for driving staples.

BACKGROUND INFORMATION

U.S. Pat. Nos. 4,540,110; 4,527,726; and 4,500,025 and U.S. Pat. No. 4,569,469 filed Feb. 15, 1985, describe generally the same types of bone stapling devices as the device described in this application and describe and claim numerous novel features of such devices which facilitate driving staples into bone portions during surgery.

Generally, the staplers described in those patents and application and in this application are adapted for use with generally U-shaped staples. The staplers comprise (1) a barrel assembly including a first housing part having a passageway extending from an inlet opening to an outlet opening, adapted to guide a single staple moved from the inlet to the outlet opening with the distal ends of its legs leading and having a socket adapted to releasably receive a cartridge containing staples at the inlet opening, and a driver having a contact end portion adapted to engage the central portion of the staple, the driver being mounted on the first housing part for sliding movement between a load position with the driver spaced from the socket and inlet opening to afford movement of one of the staples into the passageway, along the passageway with the contact end portion pushing the staple, to an eject position at which the contact end portion of the driver pushes the staple out the outlet opening while restricting rotation of the driver relative to the first housing part; (2) a handle assembly including a second housing part and drive means including a piston assembly mounted on the second housing part and adapted to be manually activated for moving the piston assembly between first and second positions; and (3) means for releasably attaching together the barrel and handle assemblies including means for releasably attaching the first and second housing parts and for releasably attaching together the piston assembly and the inner end portion of the driver so that movement of the piston assembly between its first and second position will cause corresponding movement of the driver between its load and eject position to move the staple from the inlet to the outlet opening.

While those prior art means for releasably attaching together the barrel and handle assemblies afforded using different barrel assemblies on the same handle assembly to thereby drive staples of different sizes, the design of those means caused the stapler to be more difficult to clean and required more length axially of the driver and piston assembly than might otherwise be desired. Also, the barrel assembly could only be attached so as to be oriented in one of four positions with respect to the barrel assembly, thereby greatly limiting the possible orientations of staples to be driven with respect to the hand of a user grasping the handle assembly.

DISCLOSURE OF THE INVENTION

The present invention provides means for fastening together a barrel assembly and a handle assembly on a bone stapler generally of the type described above that provides greater ease of cleaning the stapler, a shorter length for the means for fastening, and much greater ability to orient the staples to be driven with respect to the hand of a user grasping the handle assembly.

According to the present invention there is provided a bone stapler which, like the prior art staplers described above, is adapted for use with generally U-shaped staples. The stapler comprises (1) a barrel assembly including a first housing part having a passageway adapted to guide a single staple moved from an inlet to an outlet opening of the passageway with distal ends of legs on the staple leading and defining a socket adapted to releasably receive a cartridge containing staples at the inlet opening, and a driver having a contact end portion adapted to engage a central portion of the staple and being mounted on the first housing part for sliding movement between a load position with the driver spaced from the socket and inlet opening to afford movement of one of the staples into the passageway, along the passageway with the contact end portion pushing the staple, to an eject position at which the contact end portion of the driver pushes the staple out the outlet opening while restricting rotation of the driver relative to the first housing part; (2) a handle assembly including a second housing part, and drive means including a piston assembly mounted on the second housing part and adapted to be manually activated for moving the piston assembly between first and second positions; and (3) means for releasably attaching together the barrel and handle assemblies including means for attaching together the first and second housing parts and for releasably attaching together the piston assembly and the inner end portion of the driver so that movement of the piston assembly between its first and second position will cause corresponding movement of the driver between its load and eject position to move the staple from the inlet to the outlet opening.

Unlike the prior art staplers described above, however, in the stapler according to the present invention (1) the inner portion of the driver is a plate like member having an end surface and at least one opening spaced from the end surface, (2) the piston assembly includes an end portion having walls defining a transverse slot receiving the inner end portion of the driver and having at least one pin projecting from one of the walls into the slot at a position spaced from the axis of the piston assembly and in a direction generally normal to the axis of the piston assembly, the slot being shaped to afford rotational movement of the inner end portion of the driver within the slot about its axis between a release position with the pin spaced from the opening, and an engaged position with the pin positioned within the opening to provide the means for releasably attaching together the piston assembly and driver, (3) the second housing part includes a handle housing portion guiding the end portion of the piston for movement between its first and second positions while preventing relative rotation between the handle housing portion and the end portion of the piston, (4) the means for fastening together the first and second housing parts comprises structures on the housing parts adapted to be engaged at an engage position to position the end portion of the driver in the slot in the release position of the driver, and to then be relatively moved to a lock position at which the housing parts can not be moved in the axial direction of the driver and piston assembly to thereby move the driver and the end portion of the piston assembly to the engaged position, and (5) means for releasably retaining the housing portions in the lock position.

Also, in the bone stapler according to present invention, preferably the handle housing includes a second portion adapted to be grasped by a user of the stapler, and means for mounting the first handle portion on the second handle portion for relative rotation about the axis of the piston assembly and driver so that the barrel assembly can be rotated to any orientation about that axis with respect to the hand held second portion of the handle assembly and a user can orient the staple to be driven at many positions with respect to his hand.

Additionally a bone stapler according to the present invention can further include means for preventing separation of the barrel and handle assembly when the driver is not in its load position, and means for releasably locking the driver in the load position when the barrel assembly is removed from the handle assembly to thereby preclude improper operation of the stapler and facilitate its assembly, as will be explained in greater depth hereinafter.

BRIEF DESCRIPTION OF THE DRAWING

The above and additional novel features will be described with reference to the accompanying drawing wherein like numbers refer to like parts in the several views and wherein:

FIG. 1 is a top view of a bone stapler according to the present invention;

FIG. 2 is a side view of the bone stapler of FIG. 1;

FIG. 3 is an enlarged side view partially in section of the bone stapler of FIG. 1;

FIG. 4 is an enlarged sectional view taken approximately along line 4—4 of FIG. 3, and in which a release position for the end of a driver in the stapler is shown in phantom outline;

FIG. 5 is an enlarged sectional view taken approximately along lines 5—5 of FIG. 3;

FIG. 8 is an enlarged sectional view taken approximately along line 8—8 of FIG. 3.

DETAILED DESCRIPTION

Figure 7:
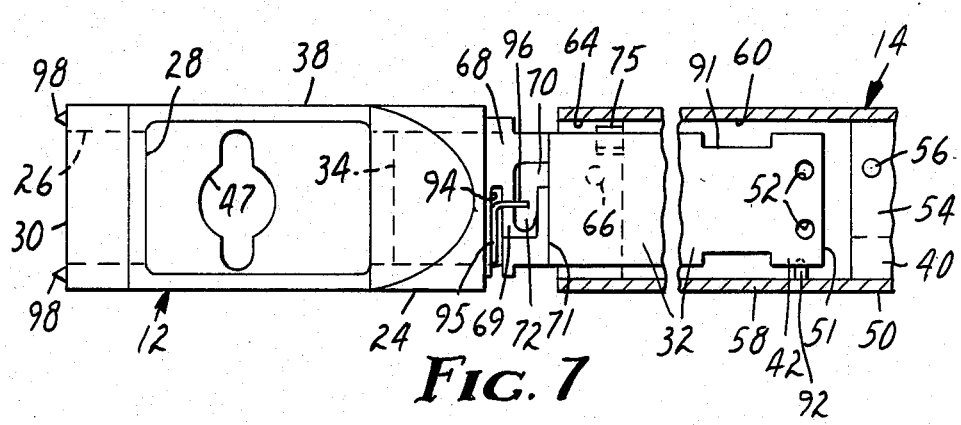
FIG. 7 is a view similar to FIG. 6 but showing the barrel assembly partially separated from the handle assembly fragment.

Referring now to the drawing there is illustrated a bone stapler according to the present invention, which stapler is generally designated by the reference numeral 10, and includes the improvements according to the present invention of (1) an improved means for attaching together a barrel assembly 12 and a handle assembly 14 included in the stapler 10, and (2) means for orienting the barrel assembly 12 from which staples 16 may be driven at a great variety of positions with respect to a portion of the handle assembly 14 adapted to be grasped by a user.

The stapler 10 is adapted for use with generally U-shaped staples 16, each comprising a central portion and two generally parallel leg portions having pointed distal ends and projecting generally in the same direction from opposite ends of its central portion. Generally the stapler 10 comprises a pistol-shaped housing 24 having a passageway 26 (FIG. 3) extending from an inlet opening 28 to an outlet opening 30, which passageway 26 is adapted to guide one of the staples 16 from the inlet opening 28 to the outlet opening 30 with the distal ends of the staple 16 leading. Means are provided for biasing a stack of the staples 16 contained in a replaceable cartridge 31 received in a socket in the housing 24 into the inlet opening 28. A driver 32 having an end portion 34 adapted to engage the central portion of one of the staples 16 is mounted on the housing 24 for sliding movement between a load position (FIG. 3) with the driver 32 spaced from the inlet opening 28 to afford movement of one of the staples 16 into the passageway 26, along the passageway 26 with its end portion 34 pushing the staple 16, to an eject position (not shown) at which the end portion 34 of the driver 32 pushes the staples 16 out of the outlet opening 30 and at which eject position the driver 32 is stopped. Drive means including an air cylinder assembly 36 powered by air under greater than atmospheric pressure and adapted to be manually activated by pulling an actuating trigger 37 into the housing 24 are provided for rapidly and forcefully propelling the driver 32 along the passageway 26 from the load position to the eject position to move the staple 16 from the inlet opening 28 to the outlet opening 30.

The driver 32 is generally blade-like with a rectangular cross section, and is guided within a close fitting opening with a rectangular cross section in a first part 38 of the housing 24.

The drive means for propelling the driver 32 comprises the air cylinder assembly 36 which includes a cylinder partially defined by a cylindrical inner surface 39 of the housing 24 concentric with the rectangular opening in which the driver 32 is guided, and a piston assembly 40 within the cylinder releasably attached to an inner end portion 42 of the driver 32 opposite its end portion 24. This piston assembly 40 includes a portion (not shown) in slidable sealing engagement with the cylindrical inner surface 39, and is movable along the inner surface 39 between a first position adjacent a first end of the cylinder opposite the driver 32 at which the piston assembly 40 is located when the driver 32 is in its load position and to which the piston assembly 40 is biased by a main spring 43 within the cylinder; and a second position adjacent a second end of the cylinder adjacent the driver 32 at which the piston assembly 40 is positioned when the driver 32 is in its eject position.

An air control system by which the piston assembly 40 is caused to move the driver 32 between its load and eject positions when the trigger 37 is pulled is not described herein, but is described in full detail in allowed U.S. patent application Ser. No. 701,970, filed Feb. 15, 1985, (for which the issue fee has been paid) now U.S. Pat. No. 4,569,469 incorporated herein by reference. That incorporated U.S. patent application Ser. No. 701,970 also fully describes and claims the cartridge 31, its interaction with the housing 24, and its novel means including a rotatable locking member 46 received in an opening 47 through the housing 24 for releasably retaining the cartridge 31 on the housing 24.

As is also fully described in the incorporated U.S. patent application Ser. No. 701,970, the bone stapler 10 also includes (1) blocking means for automatically preventing movement of the driver 32 to its load position from an intermediate position between its load and eject positions after the driver 32 has moved from its load to its eject position, at which intermediate position a portion of the driver 32 projects partially through the cartridge 31 and across the inlet opening 28 to the passageway 26. Thus, with the driver 32 initially in its load position, the drive means may be manually activated a first time by pulling the actuating trigger 37 to drive a staple 16 through the outlet opening 30 and may subsequently be manually activated an additional number of times by pulling the actuating trigger 37 so that the driver 32 will be again propelled to its eject position to further impact that driven staples 16 as may be needed to fully seat the driven staples 16, without driving an additional staple 16 from the cartridge 31; (2) reset means manually actuated by a reset trigger 48 for resetting the blocking means to allow return movement of the driver 32 from its intermediate to its load position so that another staple 16 may be driven from the cartridge 31; and (3) means including an indicating spool 49 at the end of the cylinder assembly 36 opposite the driver 32 for indicating to a user ready to fire the stapler 10 whether the driver 32 is in its load position from which a staple 16 can be driven or is in its intermediate position.

The improved means for releasably attaching together the barrel assembly 12 and the handle assembly 14 includes means for (1) releasably attaching together the first part 38 of the housing 24 included in the barrel assembly 12 and a second part 50 of the housing 24 included in the handle assembly 14 and (2) for releasably attaching together the piston assembly 40 and the inner end portion 42 of the driver 32 so that movement of the piston assembly 40 between its first and second positions will cause corresponding movement of the driver 32 between its load and eject positions to move the staple 16 from the inlet opening 28 to the outlet opening 30.

The plate-like inner end portion 42 of the driver 32 has an end surface 51 and has at least one, and as illustrated, two, openings 52 spaced from the end surface 51. The piston assembly 40 includes an end portion having walls defining a transverse end opening slot 54 receiving the inner end portion 42 of the driver 32, and having two pins 56 projecting into the slot 54 in opposite directions from opposite walls defining the slot 54 at positions spaced from the axis of the piston assembly 40 and in directions generally normal to the axis of the piston assembly 40. The slot 54 is shaped to afford rotational movement of the inner end portion 42 of the driver 32 about its longitudinal axis within the slot 54 between a release position with the pins 56 spaced from the openings 52 (shown in dotted outline in FIG. 4), and an engaged position with the pins 56 positioned within the openings 52 (shown in solid outline in FIG. 4) to provide the means for releasably attaching together the piston assembly 40 and the driver 32.

The second housing part 50 includes a first housing portion 58 guiding the end portion of the piston assembly 40 for movement between its first and second positions while preventing relative rotation between the first housing portion 58 and the end portion of the piston assembly 40 because, as is best seen in FIG. 4, the end portion of the piston assembly 40 has a generally oval periphery and is slidably guided in a passageway 60 having a corresponding uniform generally oval cross section.

The means for fastening together the first and second housing parts 38 and 50 comprises structures on the housing parts 38 and 50 adapted to be engaged at an engage position at which the inner end portion of the driver 32 is positioned in the slot 54 in the release position of the driver 32, and to then be relatively moved to a lock position at which the housing parts 38 and 50 can not be moved in a direction axial of the driver 32 and piston assembly 40 to thereby move the inner end of the driver 32 and the end portion of the piston assembly 40 to the engaged position; and releasable means operable by manually moving a button 62 are provided for releasably retaining the housing parts 38 and 50 in the lock position.

Figure 6:
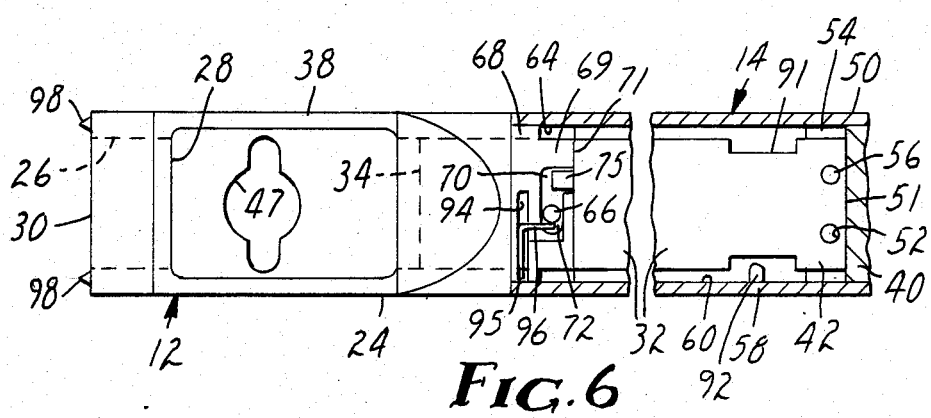
FIG. 6 is an enlarged view partially in section of a barrel assembly and a fragment of the handle assembly of the bone stapler of FIG. 1 from which a staple cartridge has been removed.
Figure 9:
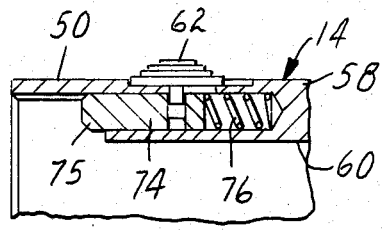
FIG. 9 is an enlarged fragmentary sectional view taken approximately along line 9—9 of FIG. 1.

The structures on the housing parts 38 and 50 adapted to be engaged comprise a cylindrical inner surface 64 on the second housing part 50, a pair of opposed radially inwardly extending projections or pins 66 attached at their outer ends to the second housing part 50 on the cylindrical inner surface 64, arcuate wall portions 68 on the first housing part 38 having outer surfaces 69 adapted for close fitting engagement with the cylindrical wall surface 64 and having generally L-shaped recesses from the outer surfaces 69 adapted to receive the projections 66. As is best seen in FIGS. 6 and 7, the L-shaped recesses each including an inlet portion 70 aligned axially of the driver 32 and opening through distal ends 71 of the arcuate wall portions 68 to receive the projections 66 at the engage position, and locking portions 72 extending circumferentially of the housing part 38 from the ends of the inlet portions 70 opposite the distal ends 71 permitting relative rotation of the housing parts 38 and 50 with the projections 66 in the locking portions 72 of the recesses to position the housing parts 38 and 50 in the lock position.

The means for releasably retaining the housing parts 35 and 50 in the lock position comprises a pin 74 fixed to the button 62 by a short connecting stem extending through a slot in the housing portion 58 to thereby mount the pin 74 on the first housing portion 58 for movement axially of the piston assembly 40 between a latched position with an end part 75 of the pin 74 positioned in the inlet portion 70 of one of the recesses when the housing parts 38 and 50 are in the lock position, and a release position spaced from the inlet portion 70 of that recess; and means in the form of a spring 76 for biasing the pin 74 to the latched position.

The bone stapler 10 according to the present invention also includes means for mounting the first housing portion 58 on a second housing portion 77 for relative rotation about the axis of the piston assembly 40 so that a user grasping a handle incorporated in the second housing portion 77 can orient the width of the staple 16 to be driven at any orientation with respect to the axis of the driver 32. That means for mounting the first housing portion 58 on the second housing portion 77, best seen in FIG. 8, comprises a generally cylindrical inner bearing surface 78 on the first housing portion 58 and a cylindrical outer bearing surface 79 on the second housing portion 77 with the bearing surfaces 78 and 79 in close fitting relationship permitting relative rotation of the surfaces 78 and 79. The housing portions 58 and 77 have opposed annular recesses 81 and 82 respectively from the surfaces 78 and 79. The recess 82 from the outer bearing surface 79 has first portions 83 of a first depth from the outer bearing surface 79 and second portions 84 of a second greater depth from the outer bearing surface 79. A plurality of retaining lugs 85 are positioned in the first portions 83 of the recess 82 from the outer bearing surface 79 and project into the recess 81 from the inner bearing surface 78, but have dimensions affording positioning of the lugs 85 fully within the second portions 84 of the recess 82 from the outer bearing surface 79. Means in the form of screws 86 threaded into the lugs 85 and having ends projecting into sockets in the second housing portion 77 are provided for releasably retaining the lugs 85 in the first portions 83 of the recess 82 from the outer bearing surface 79. The first housing portion 58 has an access opening normally filled with a frictionally fitting plug 87 affording removal of the screws 86 through the access opening, after the plug 87 is first pressed into the recess 82, to afford moving the lugs 85 into the second portions 84 of the recess 82 from the outer bearing surface 79 and then separation of the housing portions 58 and 77 by axially pulling them apart. Annular sealing rings 88 and 89 (FIG. 3) are positioned between abutted surfaces of the first and second housing portions 58 and 77 to provide a desired amount of friction to retain the first and second housing portions 58 and 77 in relative positions at which they are placed, and to restrict entry of foreign materials between the bearing surfaces 78 and 79.

The bone stapler 10 according to the present invention further includes means for preventing separation of the barrel and handle assemblies 12 and 14 when the driver 32 is in its intermediate position described above.

The inner end portion 42 of the driver 32 has a first transverse width, and the driver 32 has a narrow portion 91 (FIGS. 6 and 7) of less transverse width than the transverse width of its inner end portion 42 spaced a predetermined distance from the end surface 51. The first housing portion 58 includes a pair of opposed axially inwardly projecting pins 92 positioned to project along opposite side surfaces of the inner end portion 42 of the driver 32 when the driver 32 is in its intermediate position to then prevent rotation of the driver 32 relative to the first housing portion 58 to the release position of the driver 32 and piston assembly 40. The pins 92, however, are positioned along the narrow portion 91 of the driver 32 when the driver 32 is in its load position to then permit rotation of the driver 32 relative to the first housing piston 58 to the release position of the driver 32 and piston assembly 40 because the pins 92 do not reach the side surfaces of the driver 32 along its narrow portion 91.

The bone stapler 10 according to the present invention further includes means for releasably locking the driver 32 in the load position when the barrel assembly 12 is removed from the handle assembly 14. The driver 32 has a notch along one edge, the first housing part 38 has a slot 94 aligned with the notch when the driver 32 is in the load position, and the barrel assembly 12 includes an elongate spring 95 having one end portion fixed to the first housing part 38 and positioned in the slot 94. The spring 95 is resiliently bendable to a release position spaced from the driver 32 from a normal position engaged with the notch in the driver 32 and has a distal end portion 96 in the locking portion 72 of one of the L-shaped recesses and shaped so that the spring 95 will be deflected to the release position by movement of one of the projections 66 along the locking portion 72 of the recess to the lock position of the housing parts 38 and 50.

Operation

The operation of the bone stapler 10 by a user will now be described assuming that a cartridge 31 containing a stack of staples 16 is held in the housing 24 by the locking member 46 and the stapler 10 is connected at a coupling half 97 to a hose assembly (not shown) including a central supply of air under greater than atmospheric pressure. The user can rotate the barrel portion 12 about the axis of the driver 32 and the piston assembly 40 to orient the width of the staple 16 to be driven at any desired orientation with respect to the handle incorporated in the second housing portion 77 that he is grasping. Also, the user can utilize a pair of pointed locating members 98 fixed to the housing 24 in positions flanking the outlet opening 30 and projecting generally parallel to the axis of the driver 32 to help position and stabilize bone portions to be stapled in the same plane. When the barrel assembly is thus oriented and the bone portions are thus positioned, the stapler 10 can be activated by manually pulling the actuating trigger 37 so that air under greater than atmospheric pressure is coupled to the first end of the cylinder which will cause rapid movement of the piston assembly 40 and thereby the driver 32 (which has its end surface 51 in contact with a surface of the piston assembly 40) from its load position (FIG. 3) spaced from the staple inlet opening 28, and through the cartridge 31 to push the adjacent staple 16 in the stack along the passageway 26 to the outlet opening 30 and drive that staple 16 into adjacent portions of bone, the driver 32 being stopped at its eject position at the outlet opening 20 by engagement of the piston assembly 40 with the second end of the cylinder. As the piston assembly 40 thus is moved away from the first end of the cylinder, a plunger (not shown) will move into the cylinder under the influence of a spring so that, after the actuating trigger 37 is released and the high pressure air at the first end of the cylinder escapes and the piston assembly 40 moves back toward its first position under the influence of the main spring 43, the piston assembly 40 will be stopped against the periphery of the plunger with the end portion 34 of the driver 32 at its intermediate position extending through the cartridge 31 so that the next staple 11 in the stack of staples 22 can not move into the inlet opening 28 to the passageway 26. The user, if desired, can then again rapidly move the driver 32 to its eject position by again pulling the actuating trigger 37 as may be desired to further drive or seat the staple 16 previously driven into the bone portions.

When the user desires to drive a second staple 16, he can pull the reset trigger 48 which will move the plunger out of the cylinder so that the main spring 43 can return the piston assembly 40 to its first position and thereby the driver 32 to its load position so that subsequent activating of the drive means by the actuating trigger 37 will drive another staple 16.

If the user wishes to remove the cartridge 31 because it is empty, or to insure that the stapler 10 can not fire another staple 16, or to insert staples with different length leg portions, he may do so my manually rotating the locking member 46 to its release position with its lugs aligned with the outer portions of the opening 47, and by then pulling the cartridge 31 from the socket in the housing 24.

If the user wishes to drive staples of a different width along its central portion, he may also do that by substituting an appropriate different barrel assembly 12 for the barrel assembly 12 being used, which different barrel assembly 12 is adapted to accommodate staples 16 of that width. Such substitution is easily accomplished by (1) manually moving the button 62 against the bias of the spring 76, (2) rotating the barrel assembly 12 relative to the housing assembly 14 (which rotation is assisted by the spring 95 that then locks the driver 32 in its load position, and rotates the inner end portion 42 of the driver 32 from its engaged to its release position) and (3) pulling the barrel and handle assemblies 12 and 14 apart. Attachment of the different barrel assembly 12 is accomplished by simply (1) inserting the inner end portion 42 of the driver 32 and the arcuate wall parts 68 of the barrel assembly 12 into the oval passageway 60 and cylindrical inner surface 64 of the first housing portion so that the projections or pins 66 enter the inlet parts 70 of the L-shaped recesses and the end portion 42 enters the slot 54 in the piston assembly in their released position, and (2) rotating the barrel and handle assemblies 12 and 14 relative to each other until the end part 75 of the pin 74 enters the adjacent inlet part 70 of the recess under the influence of the spring 76 to lock the barrel and handle assemblies 12 and 14 in their lock position. Such rotation causes the projections 66 to move along the locking parts 72 of the L-shaped recesses causing the inner end portion 42 of the driver 32 and the piston assembly 40 to rotate to their engaged position with the pins 56 in the openings 52, and causes the spring 95 to be deflected to its release position out of the notch in the driver 32. The stapler 10 is then again ready for use.

The present invention has now been described with reference to one embodiment thereof. It will be appreciated that many modifications and changes can be made in the structure of the bone stapler 10 without departing from the spirit of the present invention. Thus the scope of the claims in this application should not be limited by the structure of the stapler described herein, but only by the structures described by the language of the claims and their equivalents.

I claim:

1. In a bone stapler adapted for use with generally U-shaped staples each comprising a central portion and two generally parallel leg portions projecting generally in the same direction from opposite ends of its central portion and having distal ends, said stapler comprising:
    a barrel assembly including:
        a first housing part having a passageway extending from an inlet opening to an outlet opening, said passageway being adapted to guide a single staple moved from the inlet to the outlet opening with the distal ends of its legs leading, and defining a socket adapted to releasably receive a cartridge containing staples at said inlet opening; and
        an elongate driver having an axis, an inner end portion, and an opposite contact end portion adapted to engage the central portion of said staple, said driver being mounted on said first housing part for longitudinal sliding movement between a load position with the driver spaced from the socket and inlet opening to afford movement of one of the staples into the passageway, along said passageway with said contact end portion pushing the staple, to an eject position at which the contact end portion of the driver pushes the staple out said outlet opening while restricting rotation of said driver relative to said first housing part;
    a handle assembly including:
        a second housing part; and
        drive means including a piston assembly having an axis, mounted on said second housing part, and adapted to be manually activated for moving said piston assembly between first and second positions; and
    means for releasably attaching together said barrel assembly and said handle assembly including means for releasably attaching together said first and second housing parts and for releasably attaching together said piston assembly and the inner end portion of said driver so that movement of said piston assembly between said first and second position will cause corresponding movement of said driver between said load and eject position to move said staple from said inlet to said outlet opening; the improvement wherein:
    said inner portion of said driver is plate-like, has an end surface, and has at least one opening spaced from said end surface;
    said piston assembly includes an end portion having walls defining a transverse slot receiving the inner end portion of said driver, and having at least one pin projecting from one of said walls into said slot at a position spaced from the axis of said piston assembly and in a direction generally normal to the axis of said piston assembly, said slot being shaped to afford rotational movement of said inner end portion of said driver about said axis within said slot between a release position with said pin spaced from said opening, and an engaged position with said pin positioned within said opening to provide said means for releasably attaching together said piston assembly and driver;
    said second housing part includes a first housing portion guiding the end portion of said piston assembly for movement between said first and second positions while preventing relative rotation between said handle portion and said end portion of said piston assembly;
    said means for fastening together said first and second housing parts comprises structures on said housing parts adapted to be engaged at an engage position at which said inner end portion of said driver is positioned in said slot in said release position of said driver, and to then be relatively moved to a lock position at which said housing parts can not be moved in the axial direction of said driver and piston assembly to thereby move said inner end of said driver and said end portion of the piston assembly to said engaged position; and
    means for releasably retaining said housing portions in said lock position.

2. A bone stapler according to claim 1 wherein said handle housing includes a second housing portion adapted to be manually grasped by a user, and means for mounting said first housing portion on said second housing portion for relative rotation about the axis of said piston assembly.

3. A bone stapler according to claim 1 wherein said means for mounting said first housing portion on said second housing portion for relative rotation about the axis of said piston assembly comprises a generally cylindrical inner bearing surface on one of said housing portions and a cylindrical outer bearing surface on the other of said housing portions with said bearing surfaces in close fitting relationship permitting relative rotation of said surfaces, said housing portions having opposed annular recesses from said surfaces with the recess from said outer bearing surface having first portions of a first depth from said outer bearing surface and second portions of a second greater depth from said outer bearing surface; a plurality of retaining lugs positioned in the first portions of the recess from said outer bearing surface and projecting into the recess from said inner bearing surface but having dimensions affording positioning of the lugs fully within the second portions of the recess from said outer bearing surface; and means for releasably retaining said lugs in said first portions of the recess from said outer bearing surface, one of said housing portions having an access opening affording release of said means for releasably retaining to afford moving said lugs into said second portions of the recess from said outer bearing surface and separation of said housing portions.

4. A bone stapler according to claim 1 wherein the end portion of said piston assembly includes two of said pins projecting into said slot in opposite directions on opposite sides of the axis of said piston assembly, and the inner portion of said driver has two openings spaced from said end surface and on opposite sides of the axis of said driver.

5. A bone stapler according to claim 1 wherein said structures in said housing parts adapted to be engaged comprise a cylindrical inner surface on said second housing part, a pair of opposed radially inwardly extending projections attached at their outer ends to said second housing part on said cylindrical inner surface, arcuate wall portions on said first housing part having outer surfaces adapted for close fitting engagement with said cylindrical wall surface and having generally L-shaped recesses from said outer surfaces adapted to receive said projections, said L-shaped recesses each including an inlet portion aligned axially of said driver and opening through the distal end of said arcuate wall portions to receive said projections at said engage position, and locking portions extending circumferentially from the ends of said inlet portions opposite said distal end permitting relative rotation of said housing parts with said projections in said locking portions to position said housing parts in said lock position, and said means for releasably retaining said housing parts in said lock position comprises a pin mounted on said second housing portion for movement axially of said plunger assembly between a latched position with an end part of said pin positioned in the inlet portion of one of said recesses when said housing parts are in said lock position and a release position spaced from the inlet portion of that recess, and means for biasing said pin to said latched position.

6. A bone stapler according to claim 1 further including means for releasably locking said driver in said load position when said barrel assembly is removed from said handle assembly.

7. A bone stapler according to claim 5 wherein said driver has a notch along one edge, said first housing part has a slot alligned with said notch when said driver is in said load position, and said barrel assembly includes an elongate spring having an end portion fixed to said first housing and positioned in said slot, said spring being resiliently bendable to a release position spaced from the driver from a normal position engaged with said notch and having a distal end portion in the locking portion of one of said recesses and shaped so that said spring will be deflected to said release position by movement of one of said projections along said locking portion of said recess to the lock position of said housing parts.

8. A bone stapler according to claim 1 further including blocking means for automatically preventing movement of the driver to its load position from an intermediate position between said load and eject positions wherein said stapler includes means for preventing separation of said barrel and handle assemblies when said driver is in said intermediate position.

9. A bone stapler according to claim 8 wherein the inner end portion of said driver has a first transverse width, said driver has a narrow portion of less transverse width than said first transverse width spaced a predetermined distance from said end surface, and said first housing portion includes at least one pin positioned to project along the side surface of the inner end portion of said driver when said driver is in said intermediate position to then prevent rotation of said driver relative to said first housing portion to said release position, said pin being positioned along said narrow portion of said driver when said driver is in said load position to permit rotation of said driver to said release position.

* * * * *